(12) United States Patent
Rudd

(10) Patent No.: US 9,410,143 B1
(45) Date of Patent: Aug. 9, 2016

(54) BIOLOGICAL MOLECULES PRODUCED BY ELECTROMAGNETICALLY STIMULATING LIVING MAMMALIAN CELLS

(71) Applicant: Donnie Rudd, Sugar Land, TX (US)

(72) Inventor: Donnie Rudd, Sugar Land, TX (US)

(73) Assignee: Endonovo Therapeutics, Inc., Woodland Hills, CA (US)

( * ) Notice: Subject to any disclaimer, the term of this patent is extended or adjusted under 35 U.S.C. 154(b) by 0 days.

(21) Appl. No.: 14/464,662

(22) Filed: Aug. 20, 2014

Related U.S. Application Data

(60) Provisional application No. 62/010,358, filed on Jun. 10, 2014.

(51) Int. Cl.
*C12N 13/00* (2006.01)

(52) U.S. Cl.
CPC .................................. *C12N 13/00* (2013.01)

(58) Field of Classification Search
None
See application file for complete search history.

(56) References Cited

U.S. PATENT DOCUMENTS

| | | |
|---|---|---|
| 5,155,035 A | 10/1992 | Wolf et al. |
| 5,224,922 A | 7/1993 | Kurtz et al. |
| 6,485,963 B1 | 11/2002 | Wolf et al. |
| 7,179,217 B2 | 2/2007 | Goodwin et al. |
| 7,456,019 B2 | 11/2008 | Goodwin et al. |
| 7,601,114 B2 | 10/2009 | Goodwin et al. |
| 8,029,432 B2 | 10/2011 | Dennis et al. |
| 8,137,258 B1 | 3/2012 | Dennis et al. |
| 8,137,259 B1 | 3/2012 | Dennis et al. |
| 2002/0001826 A1 | 1/2002 | Wager et al. |
| 2006/0188984 A1 | 8/2006 | Rudd et al. |
| 2006/0193836 A1 | 8/2006 | Rudd et al. |
| 2006/0193837 A1 | 8/2006 | Rudd et al. |
| 2006/0193838 A1 | 8/2006 | Rudd et al. |
| 2006/0193839 A1 | 8/2006 | Rudd et al. |
| 2007/0048253 A1 | 3/2007 | Goodwin et al. |
| 2007/0082328 A1 | 4/2007 | Rudd et al. |
| 2007/0087324 A1 | 4/2007 | Rudd et al. |
| 2007/0098699 A1 | 5/2007 | Rudd et al. |
| 2007/0117087 A1 | 5/2007 | Rudd et al. |
| 2007/0172466 A1 | 7/2007 | Rudd et al. |
| 2007/0190520 A1 | 8/2007 | Wolf et al. |
| 2008/0057042 A1 | 3/2008 | Rudd et al. |
| 2008/0075704 A1 | 3/2008 | Rudd et al. |
| 2008/0171020 A1 | 7/2008 | Rudd et al. |
| 2009/0068153 A1 | 3/2009 | Rudd et al. |
| 2009/0081751 A1 | 3/2009 | Goodwin et al. |
| 2009/0081752 A1 | 3/2009 | Dennis et al. |
| 2009/0082613 A1 | 3/2009 | Dennis et al. |
| 2010/0178680 A1 | 7/2010 | Goodwin et al. |
| 2011/0143351 A1 | 6/2011 | Rudd et al. |

OTHER PUBLICATIONS

Esposito et al. "Differentiation of Human Osteoprogenitor Cells Increases after Treatment with Pulsed Electromagnetic Fields" (2012) In Vivo, vol. 26: 299-304.*

Cleary "A review of In Vitro Studies: Low-Frequency Electromagnetic Fields" (1993) American Industrial Hygiene Association Journal, vol. 54, No. 4: 178-185.*

* cited by examiner

*Primary Examiner* — Robert Yamasaki
*Assistant Examiner* — Teresa E Knight
(74) *Attorney, Agent, or Firm* — Kelly & Krause, L.P.; W. Dennis Drehkoff

(57) ABSTRACT

The disclosure describes a method for producing native mammalian biological molecules by electromagnetically stimulating mammalian cells using an electromagnetic field. The mammalian cells can be grown in a chamber that is exposed to a time varying electromagnetic force. The biological molecules can be isolated from the cells.

2 Claims, No Drawings

BIOLOGICAL MOLECULES PRODUCED BY ELECTROMAGNETICALLY STIMULATING LIVING MAMMALIAN CELLS

The present invention relates generally to the field of production of biological molecules. Specifically, the present invention relates to a system and process for producing biological molecules by electromagnetically stimulating mammalian cells using an electromagnetic field.

Biological molecules such as granulocyte-colony stimulating factor (G-CSF), granulocyte-macrophage colony stimulating factor (GM-CSF), interleukins 2 to 32, human growth factor (HGF), leukemia inhibitory factor (LIF), erythropoietin, kinase, cytokines, interferons, tissue plasminogen activator, α1-antitrypsin, coagulation factor VIII, epidermal growth factor, and follicle stimulating hormone are extensively used in research and therapeutic treatment. It has been difficult or costly to synthesize these molecules for research or therapeutic use. For instance, G-CSF, a glycoprotein of 25 kD containing internal disulfide bonds, induces the survival, proliferation, differentiation and function of neutrophilic granulocyte precursor cells and functionally activates mature neutrophils. Among the family of colony-stimulating factors, G-CSF is the most potent inducer of terminal differentiation to granulocytes and macrophages of leukaemic myeloid cell lines. It is a protein that stimulates the growth and maturation of granulocytes. It is used to promote the recovery of the white cells following chemotherapy. The two forms of recombinant human G-CSF in clinical use (filgrastim and lenograstim) are potent stimulants of neutrophil granulopoiesis and have demonstrated efficacy in preventing infectious complications of some neutropenic states. They can be used to accelerate neutrophil recovery from myelosuppressive treatments. G-CSF also decreases the morbidity of cancer chemotherapy by reducing the incidence of febrile neutropenia, the morbidity of high-dose chemotherapy supported by marrow transplantation, and the incidence and duration of infection in patients with severe chronic neutropenia.

Mouse granulocyte colony stimulating factor (G-CSF) was first recognized and purified in Australia in 1983, and groups from Japan and the U.S.A. cloned the human form in 1986. The natural human glycoprotein exists in two forms of 174 and 177 amino acids. The more abundant and more active 174 amino acid form has been used in the development of pharmaceutical products by recombinant DNA technology.

The recombinant human G-CSF synthesized in an *E. coli* expression system is called filgrastim. The structure of filgrastim differs slightly from the natural glycoprotein. Most published studies have utilized filgrastim and it was the first form of G-CSF to be approved for marketing in Australia.

Another form of recombinant human G-CSF identified as lenograstim is synthesized in Chinese hamster ovary (CHO) cells. As this is a mammalian cell expression system, lenograstim is indistinguishable from the 174 amino acid natural human G-CSF. No clinical or therapeutic consequences of the differences between filgrastim and lenograstim have yet been identified, but there are no formal comparative studies.

G-CSF (filgrastim) is indicated for the prevention of febrile neutropenia in patients receiving myelosuppressive chemotherapy for non-myeloid malignancies. It reduces the duration and severity of post-chemotherapy neutropenia.

G-CSF (lenograstim) is also approved for use to reduce the incidence of infection associated with established cytotoxic chemotherapy.

While it is naturally produced in the human body, the isolation of human G-CSF has not been commercially achieved. Consequently, the production of G-CSF has been commercially accomplished only by synthetic means such as recombinant DNA technology producing G-CSF synthesized in an *E. coli* expression system or recombinant human G-CSF synthesized in Chinese hamster ovary (CHO) cells. Both of these "synthetic" processes are costly making the product achieved expensive and thereby creating an additional burden to the already over-burdened health care system.

There are extensive publications on techniques to increase native biological molecules in humans and laboratory animals and the therapeutic effect derived there from, and many can be found in the book *Current Drug Metabolism* by Milla et al. However, like the problem associated with obtaining commercial quantities of reasonably priced G-CSF, obtaining reasonably priced quantities of GM-CSF, cytokines, interleukins, and other desired native mammalian biological molecules has not been accomplished.

Disadvantages of using existing processes for producing native mammalian biological molecules include the problem of obtaining commercial quantities of the molecules at a reasonable cost and in a timely and efficient manner.

The present invention overcomes disadvantages of prior processes and systems and provides an efficient system for producing commercial quantities of mammalian biological molecules.

The present invention relates to a process for producing native mammalian biological molecules from mammalian cells in a carrier medium. A further aspect of the invention involves introducing mammalian cells into a chamber and rotating the chamber at speeds and for a time sufficient to grow the cells and increase the amount of natively glycosylated mammalian biological molecules. The cells are preferably exposed to an electromagnetic field, which, in a preferred embodiment of the invention, is a time-varying electromagnetic field (TVEMF).

Another aspect of this invention is to provide a composition comprising one or more of native mammalian biological molecules produced by electromagnetically stimulating living mammalian cells in accordance with the process described herein.

Still another aspect of this invention is to provide a composition comprising one or more of native mammalian biological molecules such as proteins, polypeptides, glycoproteins, cytokines, post-translational proteins, post-translational peptides, and post-translational polypeptides produced in accordance with the embodiments of this invention. In particular, this invention covers the production of IL-2, IL-6, IL-8, IL-12, G-CSF, GM-CSF, RANTES, HGF, LIF, and EPO in quantities at much higher concentrations (more than 10 times the concentration) than in human peripheral blood in a relatively short time period (10 days or less).

Still other aspects of this invention relate to compositions containing one or more of these biological molecules and use of these molecules for therapeutic purposes. It is still another object of this invention to produce a mixture of native mammalian biological molecules that can be separated into its individual component parts for later research or therapeutic use.

Other aspects, features and advantages of the present invention will be apparent from the following description of the presently preferred embodiments of the invention given for the purpose of disclosure.

SUMMARY OF THE INVENTION

Briefly, this invention comprises a method of producing native biological molecules including the molecules IL-2, IL-6, IL-8, IL-12, G-CSF, GM-CSF, RANTES, HGF, LIF, and EPO with each molecule being in a concentration of more than 10 times the concentration found in human peripheral blood, said method comprising placing human adult stem cells in a culture chamber with a culture medium and subjecting the culture to a time varying electromagnetic field consisting of a square wave having a 5-100 Hz variable duty cycle and a magnetic field of from 35-200 gauss.

DETAILED DESCRIPTION OF THE INVENTION

The following definitions are meant to aid in the description and understanding of the defined terms in the context of the present invention. The definitions are not meant to limit these terms to less than is described throughout this application. Furthermore, several definitions are included relating to TVEMF and all of the definitions in this regard should be considered to complement each other, and not construed against each other.

As used throughout this application, the term "mammalian cells" or mammalian cell composition refers to mammalian cells used or grown in accordance with an embodiment of this invention. Human adult stem cells refer to post birth cells, including cord blood cells, and are readily available from stem cell banks. They can also be obtained from peripheral blood (taken as if one would take a blood sample) by taking the blood and separating it with a centrifugal As used throughout this application, the terms "mammalian cell mixture", "mammalian cell culture", "mammalian carrier medium" and other similar terms refer to a mixture of mammalian cells with a substance that allows the cells to expand, such as a medium for growth of cells. The mammalian cells may be present in the mixture simply by mixing the mammalian cells with a substance such as a cell culture medium or cell carrier medium. Preferably, the mammalian cell mixture comprises mammalian cells and Dulbecco's medium (DMEM). Preferably, at least half of the mammalian cell mixture is a cell culture medium such as DMEM.

The term "acceptable carrier" generally refers to any substance the mammalian cells wherein the cells may survive, i.e. that is not toxic to the cells, whether prior to, during or after expansion. Such carriers are well known in the art, and may include a wide variety of substances, including substances described for such a purpose throughout this application.

The adult stem cells can be blood cells (including bone marrow, cord blood cells, perivascular cells, Wharton's jelly, or very young tissue such as circumcised foreskin. Blood cells are withdrawn from a vein providing a blood sample. They are generally then separated to a mixture rich in stem cells by centrifuging them and using the middle layer or "buffy coat".

As used throughout this application, the term "TVEMF" refers to Time Varying Electromagnetic Force.

As used throughout this application, the term "TVEMF-expanded cell" refers to a cell that has been subjected to the process of TVEMF-expansion.

As used throughout this application, the term "toxic substance" or related terms may refer to substances that are toxic to a mammalian cell, or to a patient. In particular, the term toxic substance includes dead cells (which settle to the bottom) and macrophages. Other toxic substances are known and removal of these substances from the cell mixture known.

Other statements referring to the above-defined terms or other terms used throughout this application are not meant to be limited by the above definitions, and may contribute to the definitions. Information relating to various aspects of this invention is provided throughout this application, and is not meant to be limited only to the section to which it is contained, but is meant to contribute to an understanding of the invention as a whole.

A method for producing native mammalian biological molecules is described. Mammalian cells and a carrier medium are introduced into a chamber capable of sustaining cell growth and the chamber is subjected to TVEMF of from about 5 to about 100 Hz and about 35 to about 200 gauss. These parameters are preferred. The mammalian cells and carrier medium are maintained in the growth chamber under cell growth conditions. 35-39 degrees C., 3%-7% $CO_2$. The chamber can be any type of vessel and the TVEMF is applied until the supernatant liquid or carrier medium containing the cells has a significantly increased number of cells and/or until the native mammalian biological molecules are present in a harvestable amount (at least 50 pico grams of IL2) in the carrier medium or supernatant liquid. Supernatant or carrier medium containing a mixture of native mammalian biological molecules or cells can be removed from the chamber, the cells can be lysed and then the native mammalian biological molecules can be separated into individual molecular entities or mixtures of the native mammalian biological molecules. In some cases, it may be possible to isolate the native mammalian biological molecules directly from the supernatant or carrier medium and in other cases it will be necessary to lyse the cells in order to obtain the native mammalian biological molecules. These molecular entities can be used for therapeutic purposes or for research.

In accordance with an aspect of the invention, the mammalian cells are placed in a cell culture chamber. The cell culture chamber is maintained for a period of time during which a time varying electromagnetic force is generated in the chamber by the time varying electromagnetic force source. After the cells grow resulting in increased amounts of native mammalian biological molecules, the cells and the native mammalian biological molecules are removed from the chamber.

In the process of the present invention, the cells are expanded in such manner as to maintain, or have essentially the same, three-dimensional geometry (the molecule has not been flattened or stretched it, it is same geometry as in the body) and normally the same cell-to-cell support (the chemical, hormonal, and neural interaction between the cells is not changed) and cell-to-cell geometry (cells stay in relation to each other as in the body, not bouncing off the walls of a container and into each other) as the cells prior to expansion. Typically this may be accomplished by maintaining the cells suspended in a culture or carrier medium and preventing the cells from contacting a solid surface during the cell expansion, for example by maintaining the cells in a bioreactor which rotates about a horizontal axis.

In an aspect of this invention a mixture of native mammalian biological molecules is produced by electromagnetically stimulating living mammalian cells.

In the simplest terms, a rotating TVEMF-bioreactor is the type sold by Synthecon Corp. in Houston, Tex. Instructions for operation of the bioreactor are on their web site.

Optimally, the user is advised to preferably select a rotational rate that fosters minimal wall collision frequency and intensity so as to maintain the mammalian cell three-dimensional geometry and their cell-to-cell support and cell-to-cell geometry. The preferred speed of the present invention is of from 5 to 120 RPM, preferably 10-40 RPM and more preferably from 10 to 30 RPM. The cells may also be cultured in a Petri dish or flask. The TVEMF can be produced by equipment described in U.S. Pat. Nos. 8,376,925, 8,029,432, 8,137, 258, and 8,137,259.

The mammalian cell mixture may preferably be visually assessed through the preferably transparent culture chamber and manually adjusted by using the rotational speed dial. The assessment and adjustment of the mammalian cell mixture may also be automated by a sensor (for instance, a laser), which monitors the location of the mammalian cells within a TVEMF-chamber.

Furthermore, in operation the present invention contemplates that an electromagnetic generating device is turned on and adjusted so that the square wave (pursuant to Fourier curve) output generates the desired electromagnetic field in the mammalian cell mixture-containing chamber, in a range of from 35 gauss to 300 gauss.

During the time that the cells are in the TVEMF chamber, they are preferably fed nutrients and fresh media (preferably DMEM and 5% human serum albumin), exposed to hormones, cytokines, and/or growth factors (preferably G-CSF); and toxic materials are removed. The toxic materials removed from cells in a TVEMF-chamber include the toxic granular material of dying cells and the toxic material of granulocytes and macrophages. Also, a person, for instance once a day, or once every two days manually (for instance with a syringe) insert fresh media and preferably other desired additives such as nutrients and growth factors, as discussed above, into the bioreactor, and draw off the old media containing cell wastes and toxins.

The TVEMF-expansion of the cells is controlled so that the cells preferably expand (increase in number per volume, or concentration) in a sufficient amount of time 10 days or less. As indicated above and throughout this application, TVEMF-expanded mammalian cells of the present invention have essentially the same three-dimensional geometry and cell-to-cell support and cell-to-cell geometry as naturally-occurring, non-TVEMF-expanded mammalian cells. Preferably, TVEMF-expansion is carried out in a TVEMF-bioreactor at a temperature of about 26° C. to about 41° C., and more preferably, at a temperature of about 37±2° C. for 3 days.

As various changes could be made in rotating bioreactors subjected to a time varying electromagnetic force as are contemplated in the present invention, without departing from the scope of the invention, it is intended that all matter contained in the above description be interpreted as illustrative and not limiting.

Mammalian cells for use in this invention may be collected directly or indirectly from preferably a human, or may be obtained from a depository or other repository of mammalian cells or from a commercial source or other source. The cells may be pooled. The mammalian cells may be isolated through negative separation techniques, such as but not limited to sedimentation and centrifugation. Many negative separation methods are well-known in the art. However, positive selection techniques may also be used. Methods for isolating mammalian cells are known in the art, and may be used so long as they do not lyse or otherwise irreversibly harm the desired mammalian cells. For instance, an affinity method selective for the particular mammalian cells may be used.

The collected mammalian cells must be placed into a TVEMF-chamber for TVEMF-expansion to occur. As discussed above, the term "mammalian cell mixture" comprises a mixture of mammalian cells with a substance that allows the cells to expand, such as a medium for growth of cells that will be placed in a TVEMF chamber. Cell culture media, media that allow cells to grow and expand, are well-known in the art. Preferably, the substance that allows the cells to expand is cell culture media, more preferably Dulbecco's medium. The components of the cell media must, of course, not kill or damage cells. Other components may also be added to the mammalian cell mixture prior to or during TVEMF-expansion. For instance, the mammalian cells may be placed in the bioreactor with Dulbecco's medium and further supplemented with 5% (or some other desired amount, for instance in the range of about 1% to about 10%) of human serum albumin. Other additives to the mammalian cell mixture, including but not limited to growth factor, copper chelating agent, cytokine, hormone and other substances that may enhance TVEMF cell growth may also be added to the mammalian cells outside or inside the bioreactor before being placed in the bioreactor. Preferably, the volume of mammalian cells used is about 10 ml to about 100 ml, more preferably 50 ml to about 100 ml is mixed with from about 25 ml to about 100 ml Dulbecco's medium (DMEM) and supplemented with 5% human serum albumin so that the total volume of the mammalian cell mixture is about 75 to about 200 ml when placed in the bioreactor.

The term "placed into a TVEMF chamber" is not meant to be limiting the mammalian cell mixture and may be made entirely outside of the culture chamber and then the mixture placed inside the culture chamber. Also, the mammalian cell mixture may be entirely mixed inside the bioreactor. For instance, the mammalian cell mixture may be placed in the chamber with Dulbecco's medium and supplemented with 5% human serum albumin either already in the chamber, added simultaneously to the bioreactor, or added after the mammalian cells are in the bioreactor.

Optionally, the system and process may be utilized in combination with tissue culture processes (T-flasks, rollerbottles, etc.) to produce growth of native mammalian biological molecules. In this environment, growth-promoting genes can be regulated and growth inhibitory genes can be down regulated. The effect is shown to persist over a period of time after termination of the process.

The stated mixture is a mixture found in a supernatant liquid produced by mixing a cell culture and a carrier medium together and subjecting it to the electromagnetic force until the supernatant liquid has a harvestable amount of the native mammalian biological molecules. A sample of the supernatant liquid is removed and is assayed to identify the components of the supernatant liquid. The sample can be assayed using, for example, laboratory multianalyte profiling technology. An example of such a multianalyte profiling technology is the LUMINEX system (LabMAP™), Austin, TX. well known to those skilled in the art and which permits simultaneous quantitative analysis of different proteins, peptides and DNA molecules. Multi-immunoblotting techniques and techniques that utilize antibodies or probes can be used to identify the protein, peptides, DNA and RNA components of the supernatant. After establishing the presence of the desired component in the supernatant, the protein, peptide, DNA or RNA can be separated from the supernatant using methods such as a flow cytometer or high pressure liquid chromatography. The mammalian biological material being stimulated is preferably human cells, such as progenitor cells or neuronal cells.

Lysis of the cells may be required. In cases where the desired protein is not released extracellularly a variety of methods including mechanical methods such as direct mechanical description, for example by a homogenizer or a ball mill or use of ultrasonification may be used. All of these are well known to those skilled in the art. Alternatively, the intracellular proteins may be removed from the cells by the techniques such as use of a freeze/thaw cycle, or chemical means using solvents or detergents or by biological means using enzymes. Irrespective of whether the desired protein is released from the cell by its own action or whether some external means is required, it is necessary to remove the desired protein from the resultant mixture. This can be accomplished by conventional means such as precipitation followed by gel filtration and ion exchange chromatography. All of these techniques are known to those skilled in the art.

Compositions containing one or more of the native mammalian biological molecules including proteins, peptides, polypeptides, glycoproteins, cytokines, post-translational proteins, post-translational peptides, and post-translational polypeptides produced in accordance with an aspect or embodiment of this invention can be prepared. The native mammalian biological molecules are selected from but are not limited to proteins, peptides, polypeptides, glycoproteins, cytokines, post-translational proteins, post-translational peptides, and post-translational polypeptides, including specifically G-CSF, GM-CSF, HGF, LIF, cytokines, EGF and the interleukins, such as IL-2, IL-6, IL-8 and IL-10.

A composition of the present invention may include a pharmaceutically acceptable carrier; plasma, blood, albumin, cell culture medium, growth factor, copper chelating agent, hormone, buffer or cryopreservative. "Pharmaceutically acceptable carrier" means an agent that will allow the introduction of the native molecule into a mammal, preferably a human. Such carrier may include substances mentioned herein, including in particular any substances that may be used for the mammal to which the composition will be introduced. The term "introduction" of a composition to a mammal is meant to refer to "administration" of a composition to an animal. The composition may be in a form selected from tablets, lozenges, capsules, powders, dragees, aqueous or oily suspensions, syrups, elixirs, and aqueous solutions. The nature of the composition employed will, of course, depend on the desired route of administration. The composition (with a concentration at least 10× than peripheral blood) can be administered orally, topically, rectally, nasally, transdermally, or parenterally (i.e., intramuscular, intravenous, and subcutaneous) or in any other suitable way.

The preferred method for producing the native mammalian biological molecules comprises: (a) introducing mammalian cells and a carrier medium into a Synthecon cylindrical chamber; (b) rotating the cylindrical chamber about its axis at a rotational speed sufficient to prevent the cells from substantially contacting the cylindrical walls of the cylindrical chamber; (c) continuing the rotation until native mammalian biological molecules are present in a harvestable amount in the carrier liquid; and (d) separating one or more of the native mammalian biological molecules from the carrier medium by standard separation methods such as flow cytometry.

While preferred embodiments have been herein described, those skilled in the art will understand the present invention to include various changes and modifications. The scope of the invention is not intended to be limited to the above-described embodiments.

In a preferred embodiment of the invention, normal human neuronal progenitor cells (NHNP) were pooled from three donors to diminish donor-to-donor variations in response. As controls, NHNP were grown in conventional tissue culture following standard cell culturing procedures in tissue culture flasks obtained through Clonetics Corporation, San Diego, Calif.

Cell Culture Protocols:

For two-dimensional culture, GTSF-2 medium with 10% FBS, Ciprofloxacin and Fungizone was used to culture the cells (Goodwin et al., *Exp Biol Med* (Maywood) February 1993vol. 202 no. 2 181192 Rotating Wall Vessel Coculture of Small Intestine as a Prelude to Tissue Modeling: Aspects of Simulated Microgravity). 1×PBS, Collagenase, DNase and trypsin were purchased from Clonetics San Diego, Calif., and used Corning T-75 flasks (Corning Inc., Corning, N.Y.) for initial cell culture to obtain the appropriate number of cells for each experiment. Briefly, cells to be cultured were enzymatically dissociated with the referenced reagents from T-flasks, washed once with PBS-CMF and assayed for viability by trypan dye exclusion (GIBCO, Grand Island, N.Y.). Cells were grown on 100-mm petri dishes (tissue culture treated to prevent adherence) or grown on the actual electrodes inside the petri dishes. Electrodes were made of platinum and stainless steel. Cell cultures were maintained in a humidified FormaC02incubator (Forma, Inc.) at 37° C. at $CO_2$ concentration of 6%.

For three-dimensional culture, NHNP cells were prepared as described above and an RWV was sequentially inoculated with 5 mg/ml Cytodex-3 type I collagen-coated microcarriers (Pharmacia) and freshly digested NHNP cells, yielding a cell density of 2.5.×105 cells/ml in a 55-ml vessel. Tissues were cultured for 10 days or until 3- to 5-mm diameter tissue masses formed.

Generator:

A waveform (TVEMF) generator of original design and capability was developed and used to generate the waveform in a strength of 1-6 mA (AC) square wave, 5-100 Hz variable duty cycle, which was pulse-width modulated as described in the patents stated above. NHNP cells were subjected to these magnetic fields (ELF waves) (35-200 Gauss).

Two-Dimensional Experimental Protocols:

Initially, a metal electrode (platinum and stainless steel) was placed inside a petri dish and centered. NHNP were seeded at 2.5-105 cells in 0.7 ml of media GTSF-2 medium with 10% FBS, Ciprofloxacin and Fungizone was used to culture the cells 1×PBS, collagenase, DNase and trypsin were purchased from Clonetics San Diego, Calif., and used Corning T-75 flasks (Corning Inc., Corning, N.Y.) for initial cell culture. Cells were incubated for 2 days. The second day after cell inoculation is considered day 0 of the experiment protocol. At day 0, each dish was given 15 ml of media and waveform was applied to the electrodes. Cells were fed with 15 ml of media at day 3 and with 13 ml every three days thereafter at day 6, 9, and 12. At days 14 and 17, the cells were fed again with 15 ml of media. At days 17 to 21, the cells were incubated for 10 minutes in a Collagenase/DNase cocktail, then trypsin was directly applied to the cocktail and the cells were further incubated for 3 more minutes. Before the complete media was added to deactivate the trypsin, the cocktail mix was pipetted up and down several times. The cells were washed twice with 1×PBS, reapplied with the media, and placed on ice. The cells were observed under a dissecting microscope, counted, and assessed for viability.

An identical protocol was followed in similar experiments with the exception that, instead of the electrode being placed within the petri dishes, in media, it was attached to the underside of the TVEMF treated dishes, so that the cells had no direct contact with the metal surface.

Three-Dimensional (RWV) Experimental Protocol:

Three-dimensional neural cells and tissues were cultured by the method described above, except that the TVEMF Synthecon rotating vessel was modified to incorporate an electromagnetic coil. The coil was wrapped around the core of the vessel so it emitted the same electromagnetic field strength as in the two-dimensional configuration. All other conditions were identical to the two-dimensional experimental conditions. In addition to an affimatrix survey for biomolecules, a proteonomics analysis was conducted and secretome was found in the media.

The invention claimed is:

1. A method of producing biological molecules including the molecules IL-2, IL-6, IL-8, IL-12, G-CSF, GM-CSF, RANTES, HGF, LIF, EPO and secretome with each molecule being in a concentration of more than 10 times the concentration found in human peripheral blood, said method comprising placing human adult stem cells in a culture chamber with a culture medium in a bioreactor which rotates about a horizontal axis and maintains the cells suspended in culture medium and subjecting the culture to a time varying electromagnetic field consisting of a square wave having a 5-100 Hz variable duty cycle and a magnetic field of from 35-200 Gauss.

2. A method of producing biological molecules including the molecules IL-2, IL-6, IL-8, IL-12, G-CSF, GM-CSF, RANTES, HGF, LIF, EPO and secretome with each molecule being in a concentration of more than 10 times the concentration found in human peripheral blood, said method comprising placing human adult stem cells in a culture chamber with a culture medium and culturing the cells while subjecting the culture to a time varying electromagnetic field consisting of a square wave having a 5-100 Hz variable duty cycle and a magnetic field of from 35-200 Gauss, wherein the cells are cultured in suspension in the culture medium so that the cells are prevented from contacting a solid surface of the culture chamber and the cells maintain the same three-dimensional cell-to-cell geometry throughout the culturing.

* * * * *